(12) United States Patent
Uchimoto et al.

(10) Patent No.: US 6,369,291 B1
(45) Date of Patent: Apr. 9, 2002

(54) DISPOSABLE UNDERPANTS AND METHOD OF CONTINUOUSLY PRODUCING THE SAME

(75) Inventors: Kenichi Uchimoto, Kobe; Iwao Matsuura, Osaka, both of (JP)

(73) Assignee: Toyo Eizai Kabushiki Kaisha, Kawanoe (JP)

( * ) Notice: Subject to any disclaimer, the term of this patent is extended or adjusted under 35 U.S.C. 154(b) by 0 days.

(21) Appl. No.: 09/490,289

(22) Filed: Jan. 20, 2000

Related U.S. Application Data

(63) Continuation of application No. PCT/JP98/02402, filed on May 29, 1998.

(51) Int. Cl.[7] .................... A61F 13/15; A61F 13/20
(52) U.S. Cl. ............ 604/367; 604/385.01; 604/385.27; 604/385.29; 604/375; 604/378
(58) Field of Search .............. 604/385.01, 385.24, 604/385.27, 385.28, 366, 378, 367, 385.29, 375

(56) References Cited

U.S. PATENT DOCUMENTS

| | | | | |
|---|---|---|---|---|
| 4,673,402 A | * | 6/1987 | Weisman et al. | 604/368 |
| 4,692,161 A | * | 9/1987 | Puletti et al. | 604/366 |
| 4,718,898 A | * | 1/1988 | Puletti et al. | 604/366 |
| 4,880,419 A | * | 11/1989 | Ness | 604/368 |
| 4,988,344 A | * | 1/1991 | Reising et al. | 604/368 |
| 5,134,007 A | * | 7/1992 | Reising et al. | 428/78 |
| 5,188,624 A | * | 2/1993 | Young, Sr. et al. | 604/378 |
| 5,447,508 A | * | 9/1995 | Numano et al. | 604/385.2 |
| 5,449,353 A | * | 9/1995 | Watanabe et al. | 604/385.2 |
| 5,486,167 A | * | 1/1996 | Dragoo et al. | 604/384 |
| 5,505,719 A | * | 4/1996 | Cohen et al. | 604/372 |
| 5,624,424 A | * | 4/1997 | Saisaka et al. | 604/385.2 |
| 5,669,894 A | * | 9/1997 | Goldman et al. | 604/368 |
| 5,746,731 A | * | 5/1998 | Hisada | 604/385.02 |
| 5,807,371 A | * | 9/1998 | Toyoda et al. | 604/385.1 |
| 5,833,678 A | * | 11/1998 | Ashton et al. | 604/378 |
| 5,853,402 A | * | 12/1998 | Faulks et al. | 604/378 |
| 5,865,825 A | * | 2/1999 | Schlinz | 604/385.2 |
| 5,916,206 A | * | 6/1999 | Otsubo et al. | 604/385.2 |
| 6,045,545 A | * | 4/2000 | Vandemoortele et al. | 604/385.2 |
| 6,049,916 A | * | 4/2000 | Rajala et al. | 2/400 |
| 6,083,212 A | * | 4/2000 | Kumasaka | 604/385.02 |
| 6,210,386 B1 | * | 4/2001 | Inoue | 604/385.13 |

FOREIGN PATENT DOCUMENTS

| | | |
|---|---|---|
| JP | 61-28003 | 2/1986 |
| JP | 2-74254 | 3/1990 |
| JP | 3-139349 | 6/1991 |
| JP | 7-163617 | 6/1995 |
| JP | 8-56988 | 3/1996 |
| JP | 8-196559 | 8/1996 |
| JP | 8-280739 | 10/1996 |

* cited by examiner

*Primary Examiner*—John G. Weiss
*Assistant Examiner*—Michele Kidwell
(74) *Attorney, Agent, or Firm*—Jordan and Hamburg LLP

(57) ABSTRACT

Disposable underpants 1 according to the invention has an improved sealability at the crotch of user by providing a fitting elastic member 55 and has an absorbent core 7 having an improved shape retention by providing a first nonwoven fabric 73 as an intermediate layer inside the absorbent core 7 and adhering it to the upper and lower layers thereof. Since the absorbent core needs not be heated, inexpensive disposable underpants can be produced. Further, according to an inventive production method, a step of adhering elastic members to an outer sheet 2 and a step of producing inner absorbent members 6 are separately performed, and no heating treatment is performed in the absorbent core production step. Accordingly, the disposable underpants can be produced at a remarkably higher speed.

16 Claims, 8 Drawing Sheets

(a)    (b)    (c)

DISPOSABLE UNDERPANTS AND METHOD OF CONTINUOUSLY PRODUCING THE SAME

This is a continuation of International Application PCT/JP98/02402, with an International filing date of May 29, 1998.

BACKGROUND OF THE INVENTION

The present invention relates to disposable underpants having such a shape that a waist-opening and a pair of leg-openings are provided and left and right sides are bonded in advance, and including an absorbent core which has an excellent shape retention and is easily producible, and a method for continuously producing such disposable underpants.

Since disposable underpants commercially available at present are produced under a condition that a user walks and makes physical motions while wearing them, an absorbent core is required to have a high shape retention.

Accordingly, in the prior art, a thermoplastic resin in the form of fibers and particles is mixed as a shape retaining material in addition to pulp fibers and super absorbent polymer, particles. More specifically, if such an absorbent core is heated, this thermoplastic material is melted to adhere to the pulp fibers and the super absorbent particles. Thus, the pulp fibers are adhered to each other or adhered to the super absorbent polymer particles after a heating treatment, thereby improving the shape retention of the absorbent core. Further, the soft and bulky absorbent core can be effectively maintained thin by the mixing of the thermoplastic resin and the heating adhesion treatment.

However, if the thermoplastic resin fibers, particles, etc. are not uniformly dispersed, i.e. concentrate in several locations without being uniformly dispersed in the absorbent core, this causes such a problem that portions of the absorbent core where the thermoplastic resin is concentrated hinder the dispersion and permeation of urine and/or prevent the super absorbent polymer particles from swelling upon absorbing water, thereby reducing an absorbing speed of liquid bodily wastes.

In order to produce the above absorbent core, an oven for heating an absorbent core obtained by laminating fibers needs to be prepared. A circulating hot blast oven is generally used as such an oven. However, it is difficult for the hot blast to reach the inside of the absorbent core obtained by laminating fibers to a thickness of about 10 mm, and the absorbent core has to be passed through the oven over an extended time in order to heat it until the inside thereof reaches a melting temperature of the thermoplastic resin. In order to extend the passing time in the oven, the oven itself may be enlarged. However, this results in a large-scale facility and is disadvantageous in terms of production cost. As a result, the passing speed of the absorbent core in the oven has to be slowed, which stands as a hindrance to an improvement in production efficiency.

On the other hand, the conventional disposable underpants are made of nonwoven fabric and others, also elastic members in the form of threads or strips (made of natural rubber, polyurethane, polyolefin elastomer, etc.) are provided near and around the waist-opening and the pair of leg-openings. Even if stretchable gathers are formed only around these openings, the disposable underpants cannot be worn while ensuring a sufficient sealability. Particularly, the disposable underpants provided with a bulky absorbent core does not fit a user at the lower abdomen and the buttocks and bulges out there. For example, if a person having a light problem of incontinence wears a usual garment (trousers or skirt) over disposable underpants, the disposable underpants cause his or her waist line to bulge out, which is not a preferable appearance. In view of the user's psychology, it is naturally demanded to improve the disposable underpants to have such a shape with which nobody would notice that the user is wearing them. However, if a small absorbent pad is used so that nobody would notice, a urine leak may occur. Even if no urine leak actually occurs, users have refrained from going out due to an anxiety that they might have a urine leak.

A first object of the present invention is to produce disposable underpants provided with an absorbent member which is so constructed as to have a good shape retention without mixing thermoplastic resin fibers and particles into pulp fibers and heating them. A second object of the present invention is to provide disposable underpants which fit a user sufficiently and is unlikely to let other people notice that the user is wearing them.

SUMMARY OF THE INVENTION

The present invention is directed to disposable underpants having one waist-opening and a pair of leg-opening, having-elastic members provided near the edges of the waist-and leg-openings and having the opposite sides thereof bonded, comprising an outer sheet and an inner absorbent member, wherein:

the outer sheet is provided with a waist elastic member, leg elastic members and a fitting elastic member provided between the waist elastic member and the leg elastic members, the fitting elastic member being comprised of a plurality of thread-like elastic materials in parallel with the waist elastic member, the inner absorbent member includes a permeable top sheet, an impermeable back sheet and an absorbent core accommodated between the top and back sheets, and the absorbent core includes an upper layer made of a mixture of pulp fibers and super absorbent polymer particles, an intermediate layer provided with a first nonwoven fabric, and a lower layer made of a mixture of pulp fibers and super absorbent polymer particles, the intermediate layers being adhered to the upper and lower layers by an adhesive.

Further, a method for continuously producing disposable underpants comprises the steps of:

adhering waist elastic members, leg elastic members and fitting elastic members to a continuous web of an outer sheet, producing absorbent cores by adhering upper layers made of a mixture of pulp fibers and super absorbent polymer particles and lower layers made of a mixture of pulp fibers and super absorbent polymer particles to the upper and lower surfaces of first nonwoven fabric of intermediate layers by an adhesive, producing inner absorbent members using the absorbent cores, forming a laminated assembly by adhering the inner absorbent members at specified intervals onto the continuous web of the outer sheet having the respective elastic members adhered thereto, folding the laminated assembly in two with the inner absorbent members faced inward, providing cut-away portions for the leg-openings in the laminated assembly folded in two, bonding the opposite sides of the laminated assembly folded in two, and separating the laminated assembly having its opposite sides adhered at specified intervals to form the individual disposable underpants.

DETAILED DESCRIPTION OF THE PREFERRED EMBODIMENT OF THE INVENTION

Figure 1:
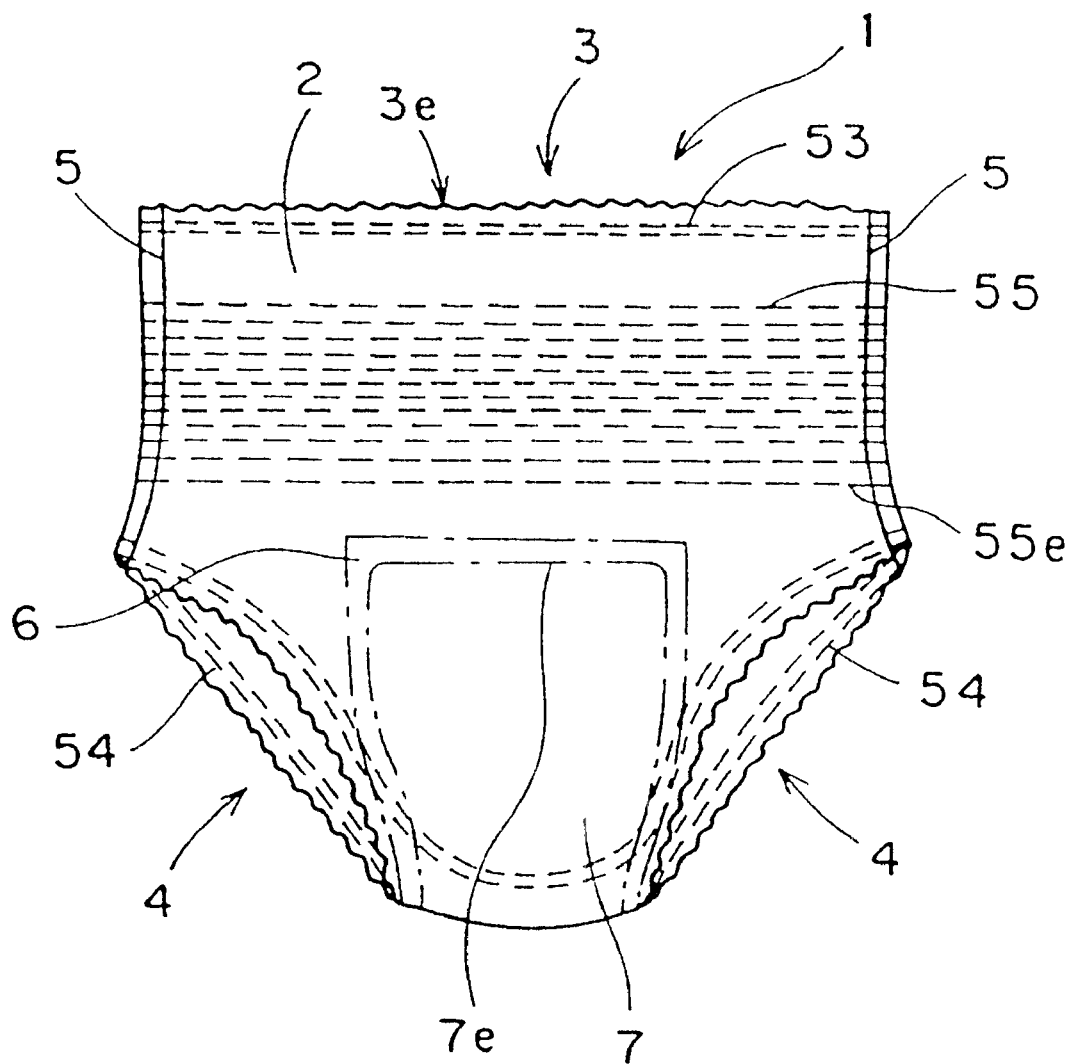
FIG. 1 is a front view of disposable underpants according to the invention.

One embodiment of disposable underpants according to the invention is described in detail with reference to FIGS. 1 to 8. Disposable underpants 1 are shaped by an outer sheet 2 to have a waist-opening 3 at the top and a pair of leg-openings 4,4 as shown in FIG. 1. Front and rear parts of the disposable underpants 1 are bonded by left and right joint portions 5. In vicinity of the waist-opening 3 and the leg-openings 4,4, a plurality of thread-shaped elastic members (polyurethane, polyolefin elastomer, rubber, etc.) are provided as a waist elastic members 53 and leg elastic members 54. These elastic members 53, 54 form waist stretchable gathers and leg stretchable gathers. Between the waist elastic member 53 and the leg elastic members 54, a plurality of thread-like elastic materials are provided as a fitting elastic member 55 in parallel to the waist elastic members 53 over the entire circumference of the disposable underpants 1. By the presence of the fitting elastic member 55, the disposable underpants 1 can fit the lower abdomen and buttocks of the user with an improved sealability.

Inside the disposable underpants 1 is mounted an inner absorbent member 6. An absorbent core 7 is contained inside the inner absorbent member 6 for absorbing bodily wastes of the user such as urine and loose stool. The positions of the fitting elastic member 55 and the absorbent core 7 are preferably adjusted so that a bottom end 55e of the fitting elastic member 55 is located more toward a waist-opening end 3e than a longitudinal end 7e of the absorbent core 7. If the fitting elastic member 55 and the absorbent core 7 overlap, the stretching force of the fitting elastic member 55 may be hindered since the absorbent core 7 is relatively hard. Further, by limiting the position of the bulky absorbent core 7 to the one below the crotch which is necessary to absorb bodily wastes, the thickness of the disposable underpants 1 at the lower abdomen and the buttocks which tend to bulge out after the disposable underpants 1 are worn can be reduced. As a result, the disposable underpants 1 can be made unnoticeable.

Figure 2:
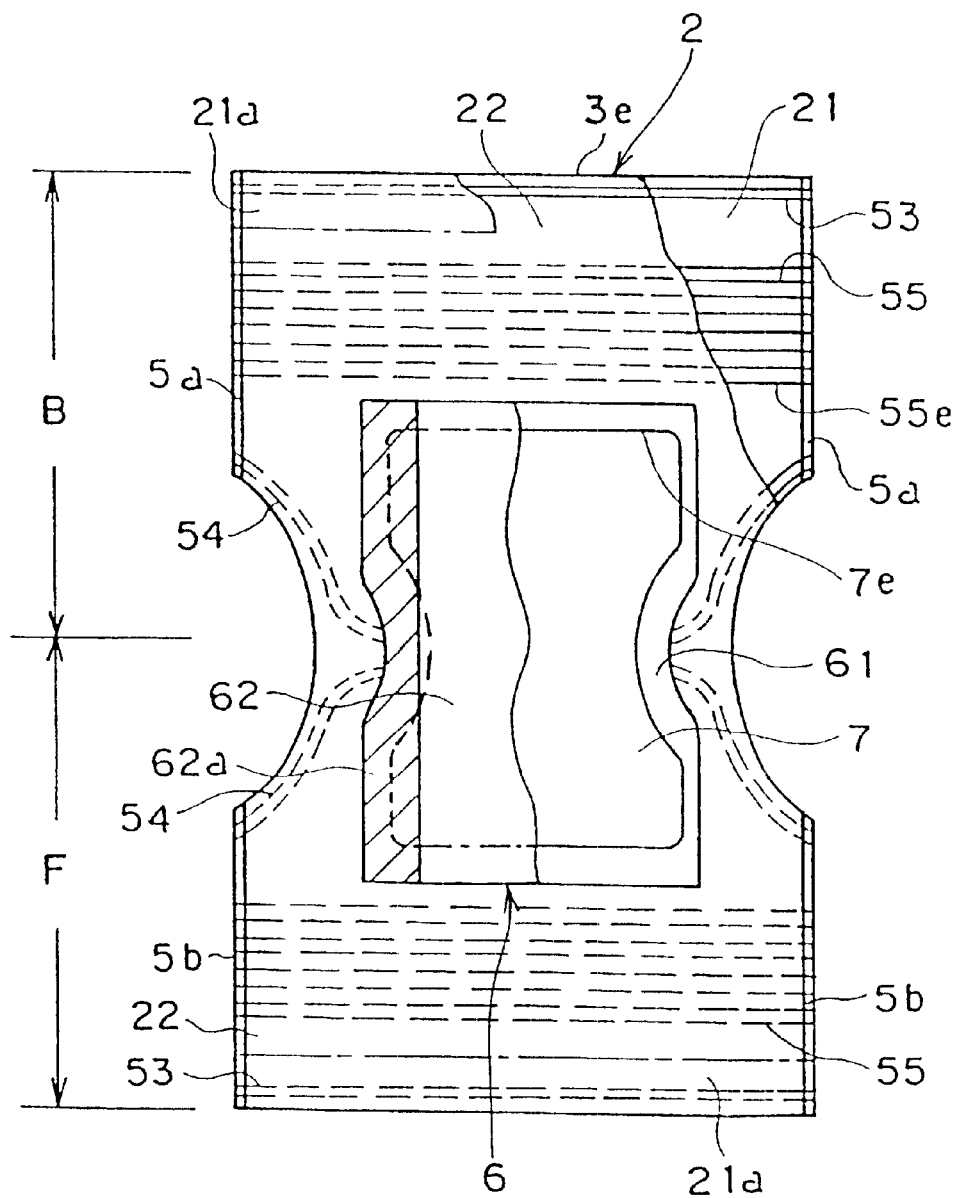
FIG. 2 is a developed plan view partly in section of the disposable underpants of FIG. 1.

FIG. 2 is a development of the disposable underpants 1 of FIG. 1. The disposable underpants 1 are substantially comprised of the outer sheet 2 and the inner absorbent member 6. The inner absorbent member 6 is bonded in the middle of the outer sheet 2, and joint margins 5a,5a at the opposite sides of a section B of the outer sheet 2 corresponding to the rear side of the disposable underpants 1 and joint margins 5b,5b at the opposite sides of a section F of the outer sheet 2 corresponding to the front side of the disposable underpants 1 are put together and joined, thereby obtaining the disposable underpants 1 having a shape as shown in FIG. 1. The outer sheet 2 is comprised of an outermost nonwoven fabric 21 and an inner nonwoven fabric 22. In an example of FIG. 2, the outermost nonwoven fabric 21 of the outer sheet 2 extends longer than the inner nonwoven fabric 22 at the waist-opening end 3e, and this projecting portion is turned down onto the inner nonwoven fabric 21, thereby forming a turned portion 21a. The waist elastic member 53 in its stretched state is intermittently adhered between the turned portion 21a and the inner nonwoven fabric 22. The fitting elastic member 55 and the leg elastic members 54 are provided between the outermost nonwoven fabric 21 and the inner nonwoven fabric 22. It should be noted that the waist elastic member 53 may be provided between the outermost nonwoven fabric 21 and the inner nonwoven fabric 22. In such a case, the turned portion 21a may or may not be provided.

Nonwoven fabrics made of cellulose, rayon, acetate, polyethylene, polypropylene, nylon, polyester, acrylic fiber, etc. (hereinafter, nonwoven fabrics are referred to as these nonwoven fabrics) can be preferably used for the outermost nonwoven fabric 21 and the inner nonwoven fabric 22 and others. Nonwoven fabrics to which a water repellent treatment is applied may be used. A hot-melt adhesive can be conveniently used to adhere the respective elastic members to the respective nonwoven fabrics.

The inner absorbent member 6 is comprised of an impermeable back sheet 61 located at the outermost in this member 6, the absorbent core 7 and a permeable top sheet 62 to fit a user's skin. The impermeable back sheet 61 may be caused to project at the left and right sides of the absorbent core 7, and the projecting portions may be turned onto the upper surface of the top sheet 62 as indicated by a hatched portion 61a in FIG. 2. This prevents urine from leaking through the opposite sides of the absorbent core 7.

Figure 3:
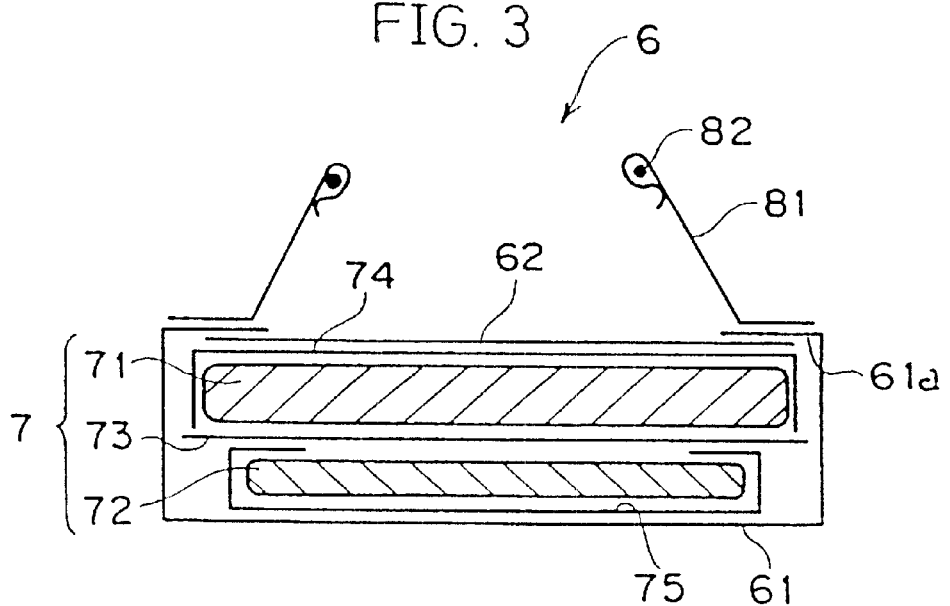
FIG. 3 is a section showing an embodiment of an inner absorbent member.
Figure 4:
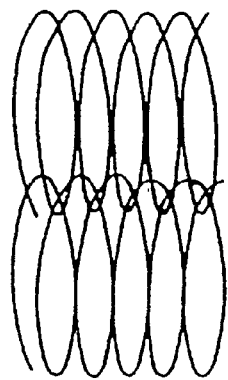
FIGS. 4(a) to 4(c) are plan views showing applied states of adhesive.
Figure 4:
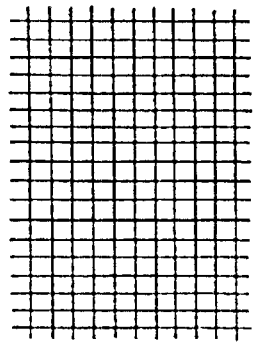
Figure 4:
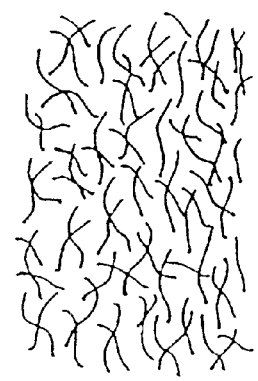

FIG. 3 is a section showing a preferable embodiment of the inner absorbent member 6 along its widthwise direction. The absorbent core 7 in the inner absorbent member 6 essentially consists of an upper layer 71, a lower layer 72 and an intermediate layer 73 including a first nonwoven fabric. The upper and lower layers 71, 72 are made of a mixture of pulp fibers and super absorbent polymer particles. The content of the super absorbent polymer particles is preferably about 10 to 65% by weight of the entire weight of the absorbing material (a total of the upper and lower layers) in order to rapidly absorb bodily wastes.

In the example of FIG. 3, a second nonwoven fabric 75 is provided below the lower layer 72 and above the impermeable back sheet 61, and a tissue 74 is provided above the upper layer 71 and below the top sheet 62. The tissue 74 and the upper layer 71; the upper layer 71 and the first nonwoven fabric 73; the first nonwoven fabric 73 and the lower layer 72; and the lower layer 72 and the second nonwoven fabric 75 are bonded to each other by a hot-melt adhesive or the like, respectively, thereby forming the absorbent core 7 as a whole.

The upper layer 71 and the first nonwoven fabric 73, and the first nonwoven fabric 73 and the lower layer 72 are bonded by applying the hot-melt adhesive to the first nonwoven fabric 73. It is preferable to bond them before the hot-melt adhesive solidifies. This is because the upper and lower layers 71 and 72 are bonded by the hot-melt adhesive permeated along the thickness direction of the first nonwoven fabric 73. Since the upper and lower layers 71,72 are firmly bonded to each other via the first nonwoven fabric 73 in the inventive absorbent core 7, the first nonwoven fabric acts as a core member, thereby giving the absorbent core 7 an excellent shape retention. Further, since the hot-melt adhesive permeates through the upper or lower layer to bond the pulp fibers to each other and the pulp fibers and the super absorbent polymer particles, this is also effective in improving the shape retention. Accordingly, if the inventive absorbent core constructed as above is used, it is not necessary to mix thermoplastic resin fibers into the absorbent core and to heat the absorbent core.

Further, by turning the side portions of the second nonwoven fabric 75 projecting from the lower layer 72 onto the lower layer 72 or by bending the tissue 74 at the opposite sides of the upper layer 71 and bonding the bent portions, the shape retention of the absorbent core 7 can be further improved. Since the tissue 74 and the second nonwoven fabric 75 can be used as a material for wrapping the upper and lower layers in a production line for the upper and lower layers 71,72, they are useful in preventing the pulp fibers and the super absorbent polymer particles from being dispersed into a working environment in the production line.

When the upper layer 71, the lower layer 72, the first nonwoven fabric 73 as an intermediate layer, the tissue 74, and the second nonwoven fabric 75 are bonded by the hot-melt adhesive, it is necessary to provide unapplied portions of the hot-melt adhesive so as not to hinder the absorption of bodily wastes such as urine and loose stool by the absorbent core 7. Particularly, unless the unapplied portions are provided in the first nonwoven fabric 73, it is not preferable since the bodily wastes do not permeates through the lower layer 72. In order to provide the unapplied portions, the hot-melt adhesive may be applied such that the applied portions form an aggregate of lines such as spirals, a net or irregular lines as shown in FIGS. 4(a), 4(b) and 4(c). It is easy to apply the melted hot-melt adhesive in such a manner as to form an aggregate of lines by applying it by the nozzle coating method, spray coating method, or the like. It should be noted that the hot-melt adhesive may be applied in strips or dots.

Figure 5:
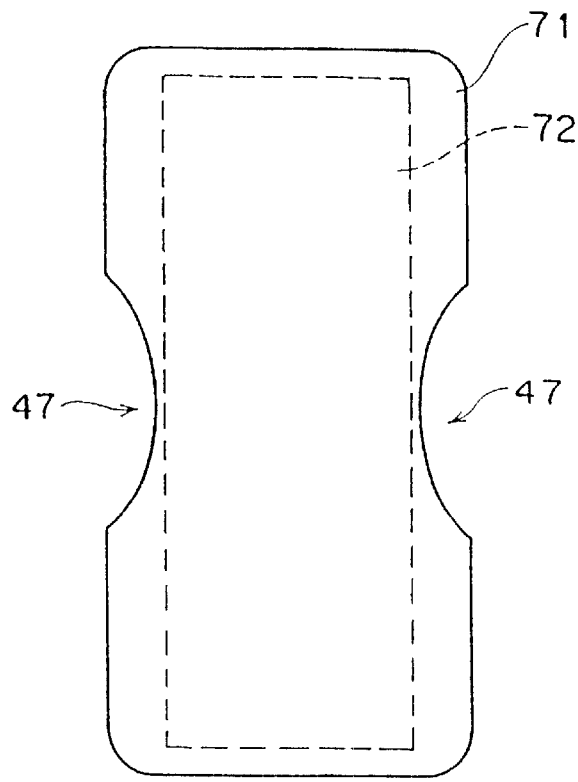
FIG. 5 is a plan view of an absorbent core.

The upper layer 71 of the absorbent core 7 is narrowed at the left and right sides in the middle with respect to its longitudinal direction to form narrow parts 47,47 so that it has a substantially sandglass-like shape as shown in FIG. 5. These narrow parts 47,47 are adapted so as not to hinder the stretchability of the leg elastic members 54,54 (see FIG. 1) of the leg-openings (identified by 4 in FIG. 1). Although the lower layer 72 may have the same shape as the upper layer 71, it preferably has a rectangular shape whose width is slightly smaller than that of the upper layer 71. Since the bodily wastes are mostly absorbed by the upper layer 71, the lower layer 72 may be provided as an auxiliary absorbing member in the case that a large amount of urine needs to be absorbed. Thus, the lower layer 72 can be made smaller than the upper layer 71. The smaller lower layer 72 reduces the bulging-out of the disposable underpants at the crotch, which makes the disposable underpants unnoticeable in appearance after being worn and prevents the stretchability of the leg gathers from being hindered. Since the human legs are normally thicker at the thighs near the crotch than at the crotch, the absorbent core is less likely to be worn or twisted due to the user's movements (rubbing of the thighs against each other) to have an improved shape retention if the lower layer 72 is made smaller.

The absorbent core 7 constructed as above is suitably bonded between the impermeable back sheet 61 and the permeable top sheet 62 as shown in FIG. 3. Of course, the top sheet 62 and the tissue 74 (the upper layer 71 when no tissue is provided) are so bonded as not to hinder the water permeability. The bottom end of raised gathers 81 may be bonded to the upper surface of the turned portion 61a which is a portion of the back sheet 61 turned onto the upper surface of the top sheet 62. By providing thread-shaped elastic members 82 at the leading ends of the raised gathers 81, the raised gathers 81 rise against the user's skin, with the result that the flow of the urine can be effectively stopped.

Figure 6:
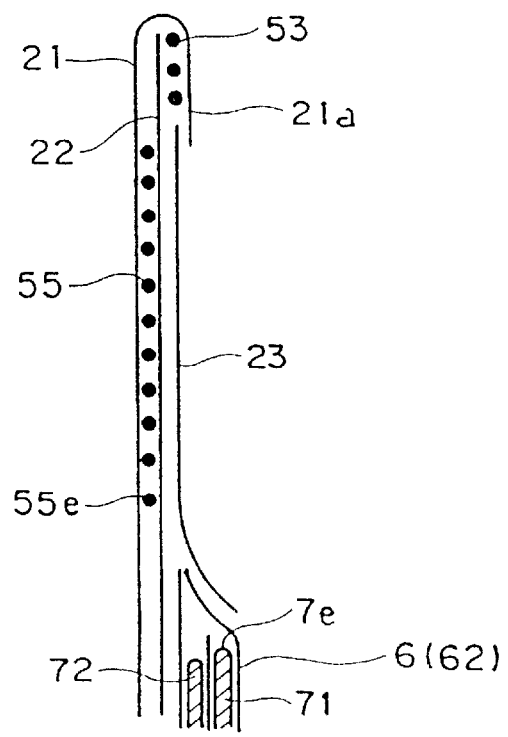
FIG. 6 is a section of the disposable underpants along their longitudinal direction.

FIG. 6 is a section of the disposable underpants along the longitudinal direction showing a preferable embodiment near the waist-opening. The outermost nonwoven fabric 21 is turned toward the inner nonwoven fabric 22 at the waist-opening edge, thereby forming the turned portion 21a as also shown in FIG. 2. The waist elastic member 53 is provided between the turned portion 21a and the inner nonwoven fabric 22. The fitting elastic member 55 is provided between the outermost nonwoven fabric 21 and the inner nonwoven fabric 22 such that its bottom end 55e is located more toward the waist-opening end (upper side in FIG. 6) than the longitudinal end 7e of the absorbent core 7 in the inner absorbent member 6. In the example of FIG. 6, a separate nonwoven fabric 23 is provided from below the turned portion 21a to the upper end of the inner absorbent member 6. This nonwoven fabric 23 is provided if necessary. If the nonwoven fabric 23 made of water repellent fibers is used or a water repellent treatment is applied to make the nonwoven fabric water impermeable, the penetration of the urine into portions of the disposable underpants outside the inner absorbent member 6 can be prevented.

In all of the above examples, the positions of the fitting elastic member 55 and the absorbent core 7 in the absorbent member 6 are adjusted such that the bottom end 55e of the fitting elastic member 55 is located more toward the waist-opening end than the longitudinal end 7e of the absorbent core 7, i.e. the fitting elastic member 55 and the absorbent core 7 do not overlap. However, the fitting elastic member 55 and the absorbent core 7 may overlap.

Figure 7:
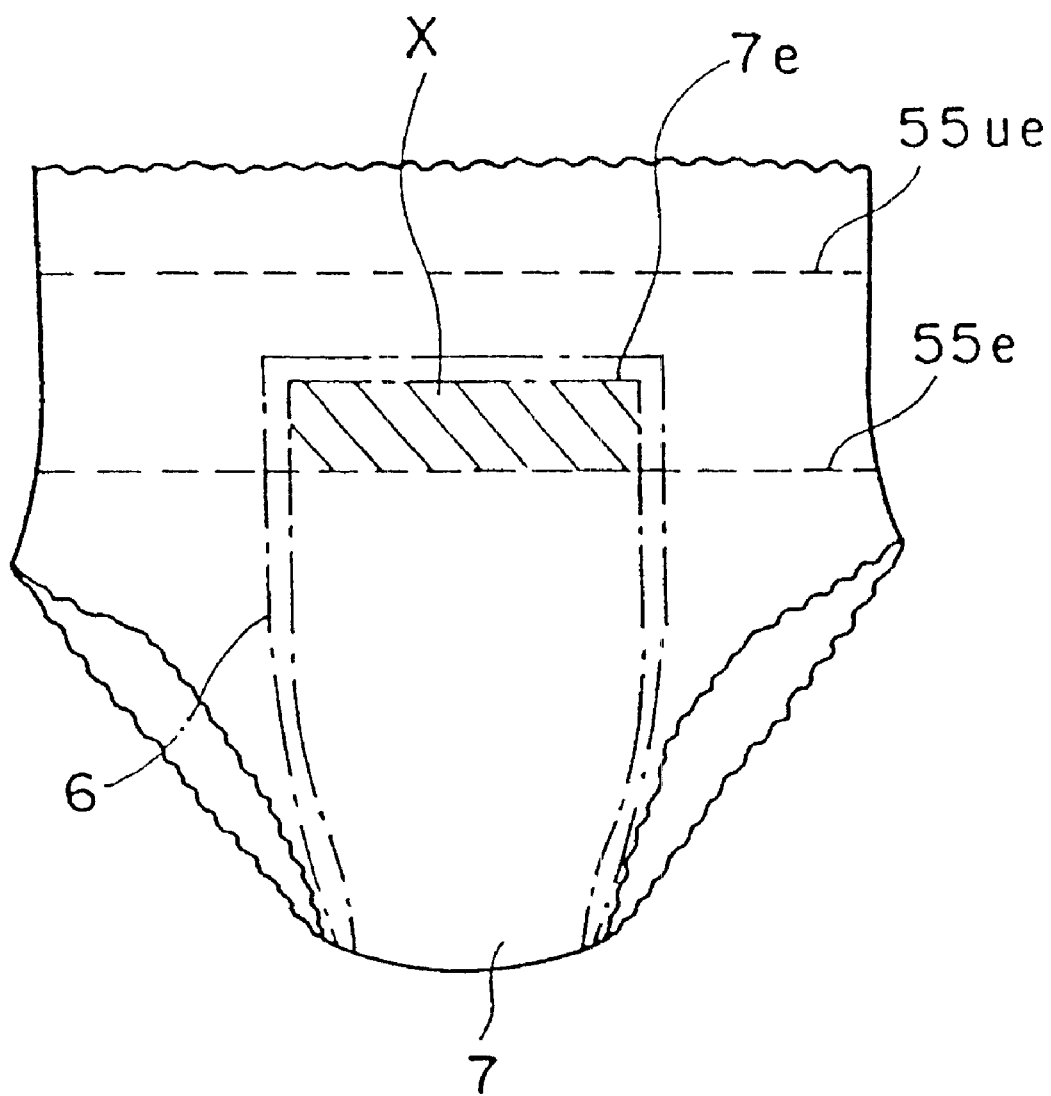
FIG. 7 is a front view showing another embodiment of the invention.

For example, FIG. 7 shows an example of disposable underpants in which the inner absorbent member 6 and the absorbent core 7 are longer than those of FIG. 1. The same elements as those shown in FIG. 1 are not shown in FIG. 7. There is an overlapping area (hatched area X) of the fitting elastic member 55 (thread-like fitting elastic materials in the order of ten are provided between the upper end 55ue and the bottom end 55e, but are not shown in FIG. 7) and the absorbent core 7. Since the absorbent core 7 is harder than the nonwoven fabric, the action of the stretchability of the fitting elastic materials on the area X does not improve the sealability of the disposable underpants, but may causes the absorbent core 7 to be worn out. However, it is complicated to cut only the fitting elastic materials overlapping with the absorbent core 7 during the production. Therefore, it is preferable to bond the fitting elastic member 55 to the outer sheet 2 without being stretched in the area X. By adopting this method, the fitting elastic member 55 can be continuously provided without being cut in the production line and there is no bad influence on the absorbent core 7 when the disposable underpants are worn.

Independent of whether the fitting elastic member overlaps the absorbent core or not, its stretching force may be changed between the front and rear sides of the disposable underpants. In the case of large-size disposable underpants frequently used by people having large buttocks, sealability can be ensured even if the stretching force of the rear side is made weaker than that of the front side, so that the buttocks are not forcibly tightened. Further, since most of the lean people have small buttocks, it is preferable to substantially equally set the stretching forces of the front and rear sides in small-size disposable underpants. Furthermore, the fitting elastic member may be provided in different positions(upper and lower portions) at the front and rear sides of the disposable underpants.

Figure 8:
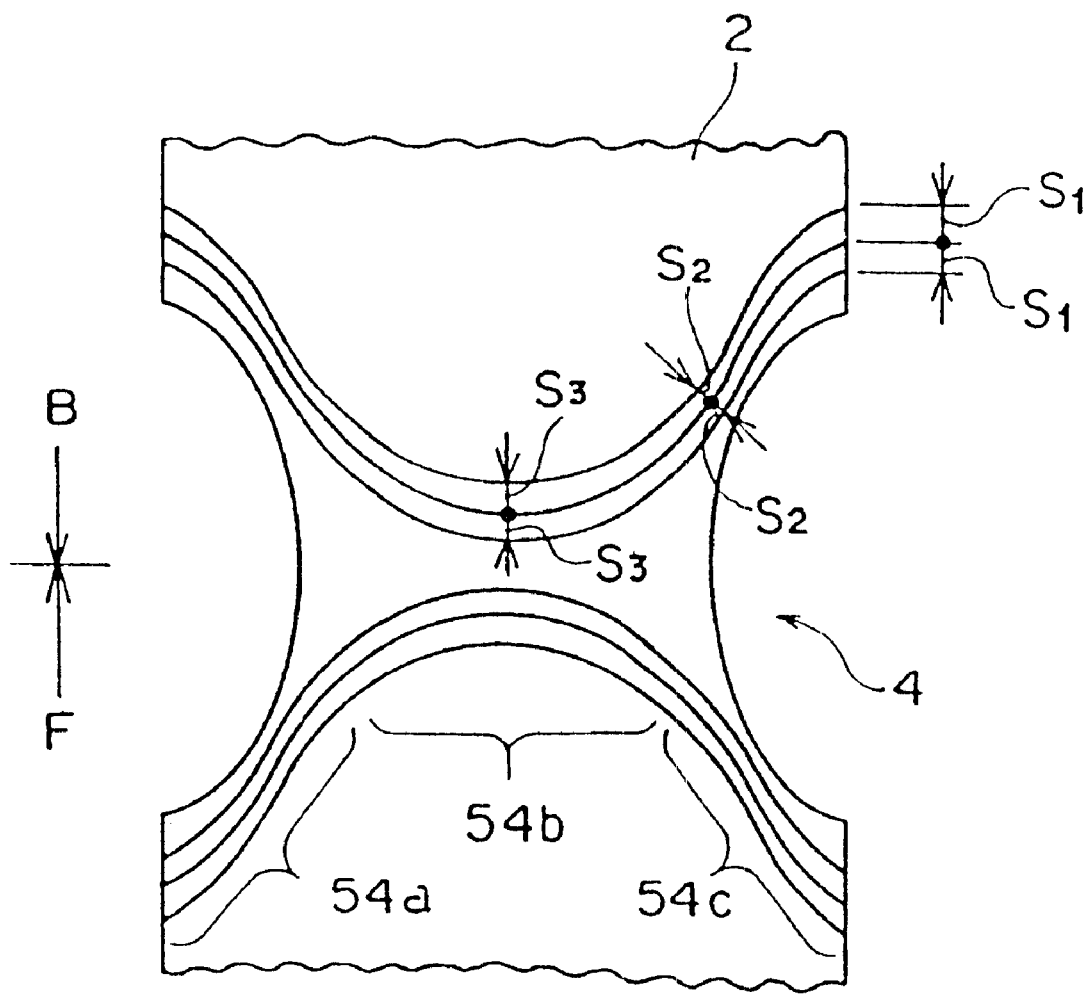
FIG. 8 is a plan view showing how leg elastic members are provided.

FIG. 8 is a diagram showing how the leg elastic members 54,54 according to the invention are provided. In the front part F of the disposable underpants, the leg elastic member 54 is comprised of left and right side portions 54a, 54c extending along the edges of the leg-openings 4,4, and a connecting portion 54b connecting the leading ends of the side portions 54a, 54c, and forms a substantially U-shaped lines. The same applies to the rear part B of the disposable underpants. As shown in FIG. 8, the connecting portions 54b of the front and rear lines of the leg elastic members 54 do not intersect with each other at the crotch of the disposable underpants. If they intersect at the crotch, the inner absorbent member 6 is squeezed outward of the disposable underpants by the stretching forces of the leg elastic members 54,54, resulting in a poor appearance. The positions of the front and rear U-shaped lines of the connecting portions 54b where they are opposed to each other may be displaced to either the front or rear part of the disposable underpants.

The spacing between the respective thread-like elastic materials forming the leg elastic members 54 is narrowest in intermediate portions ($S_2$) between the side ends of the side portions 54a (or 54c) and the middle portion of the connecting portions 54b and gradually widens toward the side ends ($S_1$) of the side portions and toward the middle portion ($S_3$) of the connecting portions 54b. Further, the thread-like elastic materials are preferably provided such that their stretching forces are weakest in the intermediate portions between the side ends of the side portions 54a (or 54c) and the middle portion of the connecting portions 54b and gradually become stronger toward the side ends ($S_1$) of the side portions and toward the middle portion ($S_3$) of the connecting portions 54b. By this construction, the crotch of the disposable underpants can closely fit the user and does not give any pain to the user by pressing his/or groin.

The disposable underpants according to the invention are formed into the shape as shown in FIG. 1 by bonding the joint margins 5a, 5b at the opposite sides of the front and rear parts in the development of FIG. 2. At this time, the joint construction at the opposite sides of the disposable underpants is such that the outer sheet 2 in which be laminated three sheets: the outermost nonwoven fabric 21, the inner nonwoven fabric 22 and the turned portion 21a, are laid one over another are put together in a portion where the turned portion 21a of the outermost nonwoven fabric 21 is present, whereas the outer sheets 2 comprised of two sheets: the outermost nonwoven fabric 21 and the inner nonwoven fabric 22, are put together in a portion where the turned portion 21a is absent (i.e. the crotch side).

Further, in the disposable underpants constructed as shown in FIG. 6, since the nonwoven fabric 23 is laid in addition to the turned portion 21a in some portion of the outer sheet, the outer sheet comprised of these is bonded. The joint margins at the opposite sides of the disposable underpants can be easily bonded using a heat sealer or an ultrasonic welding machine. If the bonding force is insufficient, an other thermoplastic film, nonwoven fabric, adhesive net, adhesive or the like may be added between any arbitrary layers to improve the bonding force.

As is clear from FIG. 1, most of the inventive disposable underpants is formed only by the outer sheet made of nonwoven fabrics, and the impermeable sheet (as 61 in FIG.1) which causes sweatiness is present only where the inner absorbent member is provided. Therefore, the inventive disposable underpants have an excellent breathability.

Figure 9:
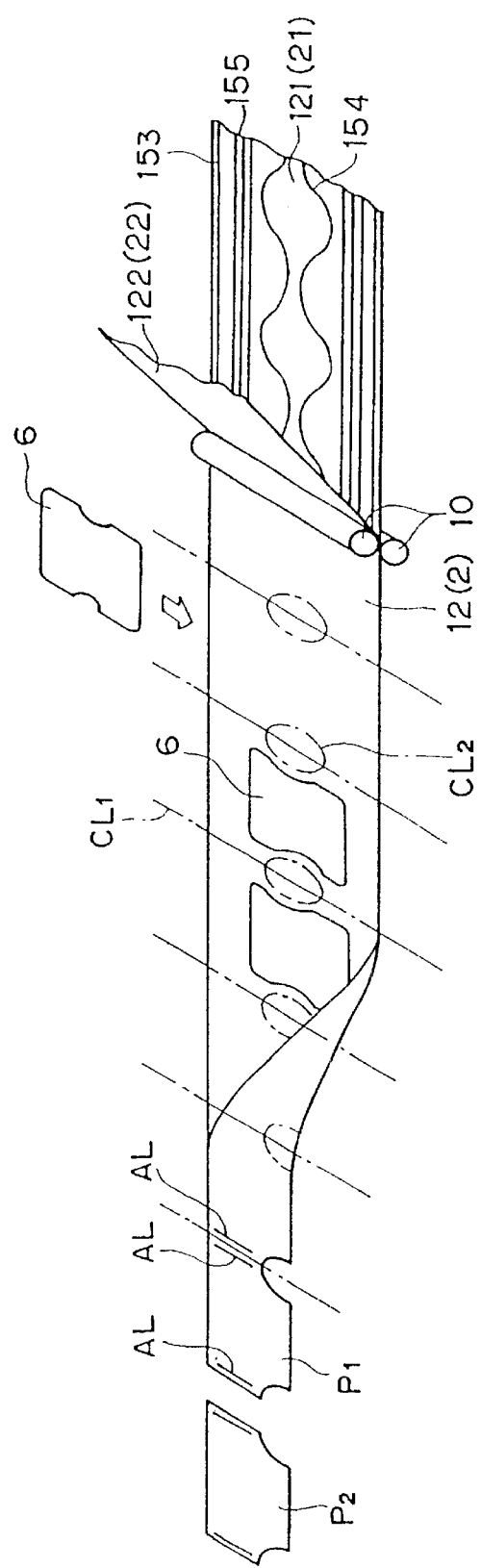
FIG. 9 is a perspective view showing a production method according to the invention.
Figure 10:
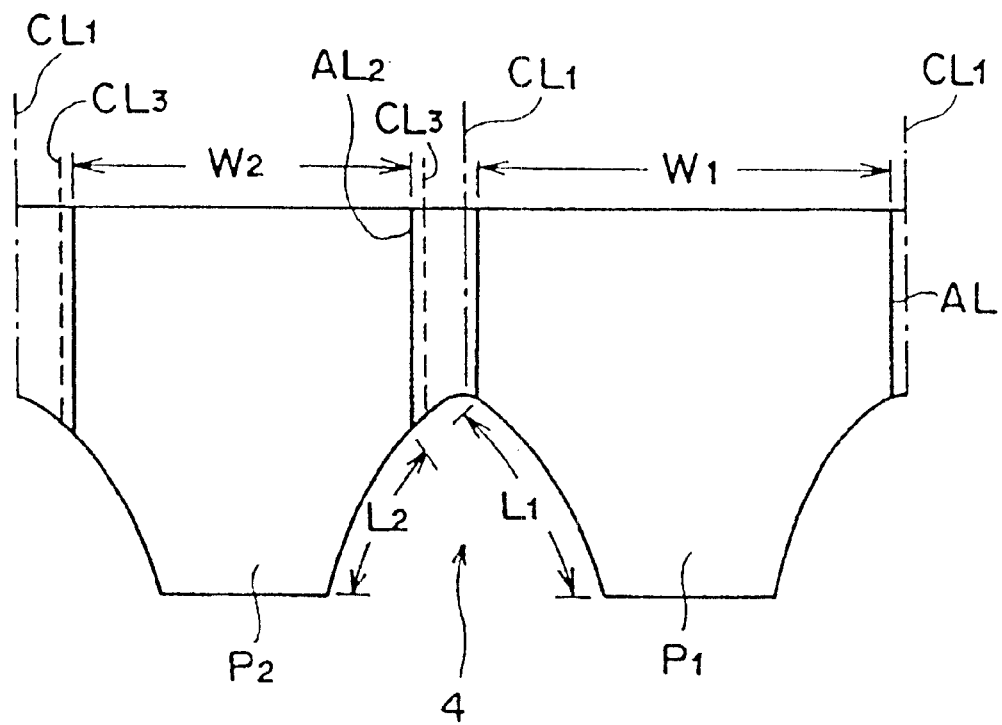
FIG. 10 is a plan view showing the production method according to the invention.

Hereinafter, a method for producing the inventive disposable underpants is described with reference to FIGS. 9 and 10. According to the inventive method, the waist elastic member, the leg elastic members and the fitting elastic member are first provided on the continuous web of the outer sheet. In FIG. 9, continuous elastic strands 153, 154 and 155 of the waist elastic member (53), the leg elastic members (54,54) and the fitting elastic member (55) are applied to a continuous web 121 of the outer nonwoven fabric (21). In this step, a hot-melt adhesive is sprayed onto the continues web 121 of the outermost nonwoven fabric (21) and/or the continuous elastic strands 153 to 155 of the respective elastic members (53 to 55), the continues elastic strands 153 to 155 are adhered to specified positions of the continues web 121 while being stretched, a continuous web 122 of the inner nonwoven fabric (22) is placed on the continuous web 121 having the continuous elastic strands 153 to 155 adhered thereto, and these continuous members 121, 153 to 155, and 122 are pressed by rollers 10,10 to adhere to each other. In order to provide the leg elastic members (54,54) in U-shaped line as shown in FIG. 8, support guides (not shown in FIG. 6) for the continuous elastic strands 154 are vertically moved in a direction normal to a running direction while the continuous web 121 is running, so that the continuous elastic strands 154 are adhered in a continuous sinusoidal curve. When the individual disposable underpants are separated, the leg elastic members 54, 54 form U-shaped lines. By this step, a continuous web 12 of the outer sheet (2) in which the respective elastic members are provided is formed.

It should be noted that a step of providing the turned portions 21a of the outermost nonwoven fabric 21 and a step of providing the another nonwoven fabric 23 can be added.

Subsequently, the inner absorbent members 6 produced in a separate step are adhered to the outer sheet continuous web 12. These inner absorbent members 6 are produced by a step of producing the absorbent core by adhering the upper and lower layers made of a mixture of the pulp fibers and the super absorbent polymer particles to the upper and lower surfaces of the first nonwoven fabric as the intermediate layer, a step of placing the top sheet on the absorbent core after the absorbent core is placed on the back sheet and rolling up the opposite sides of back sheet in such a manner as to wrap the absorbent core and adhering them to the top sheet, and, if desired, a step of adhering the members of the raised gathers. Of course, a step of adhering the tissues (74) and the second nonwoven fabric (75) shown in FIG. 3 can be added in the step of producing the absorbent core.

After the inner absorbent members 6 are adhered to the outer sheet continuous web 12 at specified intervals, a step of folding the continuous web 12 in two with the inner absorbent members 6 faced inward, a step of bonding the opposite sides of disposable underpants $P_1$, $P_1$ along bonding lines AL,AL a step of cutting along cutting lines $CL_2$ to provide cut-away portions for the leg-openings, and a step of cutting along cutting lines $CL_1$ to separate the individual disposable underpants $P_1,P_2$ are successively performed. It does not matter which of the second and the third ones of the above four steps are performed prior to the other. Alternatively, the third step may be provided before the first step.

Since the absorbent cores need not be heated according to the inventive production method, the inner absorbent members can be manufactured at a high speed. Further, the disposable underpants can be continuously manufactured at a high speed since the respective elastic members are applied in the same direction as the running direction of the continuous web of outer sheet and the folding step and the bonding step do not hinder the running of the continues web of outer sheet.

Further, according to the inventive production method, it is not necessary to prepare a producing apparatus for each size. For example, if disposable underpants $P_1$ having a large waist size $W_1$ and disposable underpants $P_2$ having a small waist size $W_2$ are produced in the same production line as shown in FIG. 10, it is sufficient to change the positions of the cutting lines $CL_1,CL_3$ and the bonding lines AL in FIG. 9. More specifically, as seen from FIGS. 9 and 10, a waist-opening length ($2 \times W_1$) of the disposable underpants $P_1$ is determined by the cutting lines $CL_1$ indicated by phantom line and the bonding lines AL (solid line) provided inside the cutting lines $CL_1,CL_1$. Further, the leg-opening length is $2 \times L_1$. The disposable underpants $P_2$ having a smaller waist width $W_2$ than $W_1$ can be easily produced by using the cutting lines $CL_3,CL_3$ (indicated by dotted line) instead of the cutting lines $CL_1,CL_1$ and defining the bonding lines $AL_2,AL_2$ inside the cutting lines $CL_3,CL_3$. Since the leg-opening length ($2 \times L_2$) of the disposable underpants $P_2$ are smaller than that of the disposable underpants $P_1$, there can be provided disposable underpants adapted to the actual situation where people having a slender waist generally have slender legs.

What is claimed is:

1. Disposable underpants comprising:
    an outer sheet having an outermost nonwoven fabric, an inner nonwoven fabric and an inner absorbent member, said outer sheet including portions defining one waist-opening, a waist-opening edge along said waist-opening, a pair of leg-openings, and left and right sides of the disposable underpants, said left and right sides each being bonded, said outermost nonwoven fabric being turned onto the inner nonwoven fabric at the waist-opening edge forming a first turned portion,
    said inner absorbent member including a permeable top sheet, an impermeable back sheet, and an absorbent core accommodated between the top sheet and the back sheet,
    said absorbent core including:
        a tissue;
        an upper layer made of a mixture of pulp fibers and super absorbent polymer particles, said tissue being above said upper layer and said upper layer formed to have a substantially sandglass-shape having narrowed portions at left and right sides of a middle portion with respect to a longitudinal direction of the absorbent core in a plan view;
        an intermediate layer provided with a first nonwoven fabric;
        a lower layer having a rectangular shape in plan view and being made of a mixture of pulp fibers and super absorbent polymer particles and portions of said lower layer defining an outer periphery of said lower layer and said intermediate layer being adhered to said upper layer and lower layer by an adhesive, said upper layer being formed larger than said lower layer and said upper and lower layer being laid such that a center line of said upper layer with respect to a widthwise direction and a centerline of said lower layer with respect to a widthwise direction correspond with each other; and
        a second nonwoven fabric below said lower layer and adhered to said lower layer, said second nonwoven fabric having a portion projecting out from the outer periphery of said lower layer such that said portion of the second nonwoven fabric is turned up onto said lower layer and adhered while being placed to the first nonwoven fabric;
    a waist elastic member provided between the inner nonwoven fabric and the first turned portion;
    leg elastic members; and
    a fitting elastic member provided between the waist elastic member and the leg elastic members, said fitting elastic member comprising a plurality of thread-like elastic materials parallel to the waist elastic member, said fitting elastic member being provided closer to the waist-opening edge than a longitudinal end of the absorbent core of the inner absorbent member such that the fitting elastic member and the absorbent core do not overlap;
    wherein at least the leg elastic members and the fitting elastic member are provided between the outermost nonwoven fabric and inner nonwoven fabric of the outer sheet.

2. Disposable underpants according to claim 1, wherein the first nonwoven fabric of the intermediate layer of the absorbent core includes an adhesive applied portion and an adhesive unapplied portion, and the adhesive applied portion forms an aggregate of a multitude of lines.

3. Disposable underpants comprising:
    an outer sheet having an outermost nonwoven fabric, an inner nonwoven fabric and an inner absorbent member, said outer sheet including portions defining one waist-opening, a waist-opening edge along said waist-opening, a pair of leg-openings, and left and right sides of the disposable underpants, said left and right sides each being bonded, said outermost nonwoven fabric being turned onto the inner nonwoven fabric at the waist-opening edge forming a first turned portion,
    said inner absorbent member including a permeable top sheet, an impermeable back sheet, and an absorbent core accommodated between the top sheet and the back sheet,
    said absorbent core including:
        a tissue;
        an upper layer made of a mixture of pulp fibers and super absorbent polymer particles, said tissue being above said upper layer and said upper layer formed to have a substantially sandglass-shape having narrowed portions at left and right sides of a middle portion with respect to a longitudinal direction of the absorbent core in a plan view;
        an intermediate layer provided with a first nonwoven fabric;
        a lower layer having a rectangular shape in plan view and being made of a mixture of pulp fibers and super absorbent polymer particles and portions of said lower layer defining an outer periphery of said lower layer and said intermediate layer being adhered to said upper layer and lower layer by an adhesive, said upper layer being formed larger than said lower layer and said upper and lower layer being laid such that a center line of said upper layer with respect to a widthwise direction and a centerline of said lower layer with respect to a widthwise direction correspond with each other; and a second nonwoven fabric below said lower layer and adhered to said lower layer, said second nonwoven fabric having a portion projecting out from the outer periphery of said lower layer such that said portion of the second nonwoven fabric is turned up onto said lower layer and adhered while being placed to the first nonwoven fabric;

a waist elastic member provided between the inner nonwoven fabric and the first turned portion;

leg elastic members; and a fitting elastic member provided between the waist elastic member and the leg elastic members, said fitting elastic member comprising a plurality of thread-like elastic materials parallel to the waist elastic member, said fitting elastic member partly overlapping an absorbent core of the inner absorbent member thereby forming an overlapping portion, a portion of said fitting elastic member located in the overlapping portion being provided in a non-stretched state so as not to contract;

wherein at least the leg elastic members and the fitting elastic member are provided between the outermost nonwoven fabric and inner nonwoven fabric of the outer sheet.

4. Disposable underpants according to claim 3, wherein the first nonwoven fabric of the intermediate layer of the absorbent core includes an adhesive applied portion and an adhesive unapplied portion, and the adhesive applied portion forms an aggregate of a multitude of lines.

5. Disposable underpants comprising:

an outer sheet having an outermost nonwoven fabric, an inner nonwoven fabric and an inner absorbent member, said outer sheet including portions defining one waist-opening, a waist-opening edge along said waist-opening, a pair of leg-openings, and left and right sides of the disposable underpants, said left and right sides each being bonded, said outermost nonwoven fabric being turned onto the inner nonwoven fabric at the waist-opening edge forming a first turned portion;

said inner absorbent member including a permeable top sheet, an impermeable back sheet, and an absorbent core accommodated between the top sheet and the back sheet, said absorbent core including:
  an upper layer made of a mixture of pulp fibers and super absorbent polymer particles;
  an intermediate layer provided with a first nonwoven fabric; and
  a lower layer made of a mixture of pulp fibers and super absorbent polymer particles, said intermediate layer being adhered to the upper layer and lower layer by an adhesive;

a waist elastic member provided between the inner nonwoven fabric and the first turned portion;

leg elastic members, each of which is made of a plurality of thread-like elastic materials, said thread-like elastic materials being located at a front part of the disposable underpants and including left and right side portions extending along leg-opening edges of the front part of the disposable underpants and connecting portions connecting leading ends of the left and right side portions, thereby forming substantially U-shaped lines and said thread-like elastic materials defining at a rear part of the disposable underpants left and right side portions extending along leg-opening edges of the rear part of the disposable underpants and connecting portions connecting leading ends of the side portions, thereby forming substantially U-shaped lines, such that the connecting portions of the front and rear parts do not intersect with each other at a crotch of the disposable underpants; and a fitting elastic member provided between the waist elastic member and the leg elastic members, said fitting elastic member comprising a plurality of thread-like elastic materials parallel to the waist elastic member, said fitting elastic member being provided closer to the waist-opening edge than a longitudinal end of the absorbent core of the inner absorbent member such that the fitting elastic member and the absorbent core do not overlap;

wherein at least the leg elastic members and the fitting elastic member are provided between the outermost nonwoven fabric and inner nonwoven fabric of the outer sheet.

6. Disposable underpants according to claim 5, wherein spacing between the respective thread-like elastic materials of each leg elastic member is narrowest at intermediate positions between side ends of the side portions and a middle of the connecting portions and gradually widens toward the side ends of the side portions and gradually widens toward the middle of the connecting portions.

7. Disposable underpants according to claim 5, wherein a stretching force of the thread-like elastic materials of the leg elastic members is weakest at intermediate positions between side ends of the side portions and a middle of the connecting portions and gradually becomes stronger toward the side ends of the side portions and toward a middle of the connecting portions.

8. Disposable underpants according to claim 5, wherein a stretching force of the fitting elastic member differs in a front part of the disposable underpants from a rear part of the disposable underpants.

9. Disposable underpants according to claim 5, wherein left and right side ends of the impermeable back sheet of the inner absorbent member are turned up onto an upper surface of the permeable top sheet forming turned portions, and raised gathers made of a nonwoven fabric and provided with a stretchable member are adhered onto the upper surface of the turned portions.

10. Disposable underpants according to claim 5, wherein the left and right sides of the disposable underpants are bonded at a left joint margin of front and rear parts and at a right joint margin of the front and rear parts, and heat-sealed thereat.

11. Disposable underpants comprising:

an outer sheet having an outermost nonwoven fabric, an inner nonwoven fabric and an inner absorbent member, said outer sheet including portions defining one waist-opening, a waist-opening edge along said waist-opening, a pair of leg-openings, and left and right sides of the disposable underpants, said left and right sides each being bonded, said outermost nonwoven fabric being turned onto the inner nonwoven fabric at the waist-opening edge forming a first turned portion;

said inner absorbent member including a permeable top sheet, an impermeable back sheet, and an absorbent core accommodated between the top sheet and the back sheet, said absorbent core including:
- an upper layer made of a mixture of pulp fibers and super absorbent polymer particles,
- an intermediate layer provided with a first nonwoven fabric, and
- a lower layer made of a mixture of pulp fibers and super absorbent polymer particles, said intermediate layer being adhered to the upper layer and lower layer by an adhesive;

a waist elastic member provided between the inner nonwoven fabric and the first turned portion;

leg elastic members, each of which is made of a plurality of thread-like elastic materials, said thread-like elastic materials being located at a front part of the disposable underpants and including left and right side portions extending along leg-opening edges of the front part of the disposable underpants and connecting portions connecting leading ends of the left and right side portions, thereby forming substantially U-shaped lines and said thread-like elastic materials defining at a rear part of the disposable underpants left and right side portions extending along leg-opening edges of the rear part of the disposable underpants and connecting portions connecting leading ends of the side portions, thereby forming substantially U-shaped lines, such that the connecting portions of the front and rear parts do not intersect with each other at a crotch of the disposable underpants; and a fitting elastic member provided between the waist elastic member and the leg elastic members, said fitting elastic member comprising a plurality of thread-like elastic materials parallel to the waist elastic member, said fitting elastic member partly overlapping an absorbent core of the inner absorbent member thereby forming an overlapping portion, a portion of said fitting elastic member located in the overlapping portion being provided in a non-stretched state so as not to contract;

wherein at least the leg elastic members and the fitting elastic member are provided between the outermost nonwoven fabric and inner nonwoven fabric of the outer sheet.

12. Disposable underpants according to claim 11, wherein spacing between the respective thread-like elastic materials of each leg elastic member is narrowest at intermediate positions between side ends of the side portions and a middle of the connecting portions and gradually widens toward the side ends of the side portions and gradually widens toward the middle of the connecting portions.

13. Disposable underpants according to claim 11, wherein a stretching force of the thread-like elastic materials of the leg elastic members is weakest at intermediate positions between side ends of the side portions and a middle of the connecting portions and gradually becomes stronger toward the side ends of the side portions and toward a middle of the connecting portions.

14. Disposable underpants according to claim 11, wherein a stretching force of the fitting elastic member differs in a front part of the disposable underpants from a rear part of the disposable underpants.

15. Disposable underpants according to claim 11, wherein left and right side ends of the impermeable back sheet of the inner absorbent member are turned up onto an upper surface of the permeable top sheet forming turned portions, and raised gathers made of a nonwoven fabric and provided with a stretchable member are adhered onto the upper surface of the turned portions.

16. Disposable underpants according to claim 11, wherein the left and right sides of the disposable underpants are bonded at a left joint margin of front and rear parts and at a right joint margin of the front and rear parts, and heat-sealed thereat.

* * * * *